United States Patent [19]
Franchi

[11] Patent Number: 6,030,336
[45] Date of Patent: Feb. 29, 2000

[54] PRESSURE GENERATOR FOR A COUNTERPRESSURE CARDIAC ASSISTANCE DEVICE

[75] Inventor: Pierre Franchi, Vitry-sur-Seine, France

[73] Assignee: Synthelabo Biomedical (Société Anonyme), Le Plessis-Robinson, France

[21] Appl. No.: 09/125,683
[22] PCT Filed: Feb. 19, 1997
[86] PCT No.: PCT/FR97/00303
  § 371 Date: Dec. 11, 1998
  § 102(e) Date: Dec. 11, 1998
[87] PCT Pub. No.: WO97/30740
  PCT Pub. Date: Aug. 28, 1997

[30] Foreign Application Priority Data

Feb. 21, 1996 [FR] France .................................. 96/02136

[51] Int. Cl.[7] .................................................. A61N 1/362
[52] U.S. Cl. ............................................... 600/18; 600/16
[58] Field of Search ......................................... 600/16, 18

[56] References Cited

U.S. PATENT DOCUMENTS

| | | | |
|---|---|---|---|
| 4,439,186 | 3/1984 | Kuhl | 600/18 |
| 4,938,766 | 7/1990 | Jarvik | 623/3 |
| 5,814,102 | 9/1998 | Guldner et al. | 600/16 |
| 5,924,975 | 7/1999 | Goldowsky | 600/16 |

FOREIGN PATENT DOCUMENTS

| 239-723 | 8/1986 | Germany | 600/16 |

*Primary Examiner*—William E. Kamm
*Assistant Examiner*—Carl H. Layno
*Attorney, Agent, or Firm*—Jacobson, Price, Holman & Stern, PLLC

[57] ABSTRACT

A pump comprises variable volume means inserted in an artery, in particular, the descending aorta, enabling the volume through which the blood flows in this location to be modified cyclically and in a controlled manner. The device comprises a deformable enclosure in fluid communication with the variable volume. The variable volume and a spring coil urge the deformable enclosure against an increase of volume resulting from a pressure increase in the variable volume, and in the corresponding enclosure, in a way which produces additional elastance for the artery during the heart cycle. In addition, an electric motor can control the deformable enclosure to increase or decrease its volume, and can exert its force in addition to or in subtraction from the force of the spring coil during the systolic and diastolic phases of the heart cycle. This produces an additional pumping effect on arterial blood and correspondingly relieves the effort required of the heart.

7 Claims, 4 Drawing Sheets

PRESSURE GENERATOR FOR A COUNTERPRESSURE CARDIAC ASSISTANCE DEVICE

The invention relates to a pressure generator/regulator device for an implantable heart-assist pump of the back-pressure balloon type.

The technique using an intra-aortic back-pressure balloon is well known for providing effective hemodynamic assistance to the left ventricle in the event of congestive heart failure: the balloon is inserted in the down branch of the aorta and is inflated during the diastolic phase of the heart cycle, and as a result injects an additional volume of blood into the network of arteries both upstream and downstream from its position. Deflated during the following heart systole, it decreases the load on the left ventricle thus enabling blood flow rate to be increased. The hemodynamic balance is positive: an increase in the injection fraction; a decrease in the telediastolic pressure. Thus, the balloon delivers additional energy which the ventricle is not able to supply, and the state of the patient is very significantly improved.

Implanted systems have already been proposed which make it possible to implement that technique in an entirely self-contained manner, for example as described in U.S. Pat. No. 5,222,980, or indeed in French application 96/00949 filed on Jan. 26, 1996 belonging to the same proprietor as the present application and entitled Pompe d'assistance cardiaque implantable du type à ballonnet de contrepression [An implantable heart-assist pump of the back-pressure balloon type].

Both of those documents describe a permanent implantable heart-assist pump inserted in the descending aorta, operating on the above-mentioned principle of a back-pressure balloon constituted by a flexible and elastic membrane in the form of a sleeve whose axis coincides with that of the aorta and which is put in the place of a segment of aorta that has been removed. The membrane is contained in a rigid chamber having substantially the same shape as the membrane at rest, and into which a hydraulic fluid is injected from an external generator, thereby compressing the membrane and thus reducing the volume of blood that it contains. Conversely, extracting the hydraulic fluid causes the inside volume of the membrane to increase, and thus the pump to be filled.

More precisely, in such a system, the present invention provides a generator for controlling variations in the pressure of the hydraulic fluid, and thus for controlling the operation of the pump.

One of the objects of the invention is to provide a generator structure which optimizes the overall energy balance of the pump firstly to limit the consumption of energy by the implanted appliance, and secondly and above all to make the pump operate in as physiological manner as possible by generating blood flow in the cardiovascular system as a whole having characteristics that are as close as possible to those of a healthy organism. It can be seen below that the generator of the invention makes it possible to achieve these objects while, mechanically speaking, it remains simple, robust, and compact in structure, which characteristics are essential for a system that is implanted.

In another aspect, it can also be seen that the device of the invention can be used in a purely passive manner, i.e. without delivering net additional energy to the system (it does not have drive means, or said means are inactive), the heart providing all of the energy demand on its own. Under such circumstances, it is shown that the device of the invention nevertheless makes it possible to modify in advantageous manner the pressure wave while behaving essentially as additional elastance (elasticity factor) serving, for example, to compensate for deterioration in the natural elasticity of the arterial network.

Under such circumstances, the device of the invention behaves essentially as a pressure regulator, and that is why the general term "generator/regulator devices" is used to cover both possible ways of implementing the invention, respectively actively and passively. It will also be observed that the same device can be used at different times either in active mode or in passive mode, e.g. by being switched into active mode during phases of activity, and into passive mode during rest phases.

To achieve the above objects, the invention provides a pressure generator/regulator device for an implantable heart-assist pump of the back-pressure balloon type of the above-specified type, i.e. having variable volume means inserted in an artery, in particular the descending aorta, and making it possible to modify cyclically and in controlled manner a volume through which the blood flows in this location, the device being characterized in that it includes a deformable enclosure in fluid communication with said variable volume, and spring-forming means for urging the deformable enclosure against an increase of volume resulting from an increase in pressure in said variable volume, and correspondingly in the enclosure, so as to provide additional elastance to the artery during the heart cycle.

According to various advantageous characteristics:

the deformable enclosure is defined by a piston movable in a body, the spring-forming means urging the piston in the body in its direction for reducing the volume of the enclosure, and the piston is movable between two positions, a maximum volume position associated with maximum compression of the spring, and a minimum volume position associated with minimum compression of the spring;

motor means are provided for urging the deformable enclosure in controlled manner in the direction for increasing the volume of the enclosure or in the opposite direction, and exerting its action in addition to or in opposition to the action of the spring-forming means during the systolic phase and the diastolic phase of the heart cycle, so as to produce an additional pumping effect on the arterial blood and correspondingly relieve the effort required of the heart;

in which case, motor means are disposed inside the body, and comprise a rotary motor co-operating with a rod secured to the piston via a transmission reversibly transforming the rotary motion of the rotary motor into linear translation motion of the rod;

the transmission has a radial finger secured to the rotor of the rotary motor and co-operating with a helical groove formed in a cylindrical element of the piston rod;

the rotary motor is an electric motor of the torque motor type; and the body houses a sealed assembly with a rigid front wall forming said piston and a side wall in the form of a bellows, said sealed assembly itself enclosing the rod of the piston, the rotary motor, the transmission, and the spring-forming means.

Other characteristics of the invention appear on reading the following description of an embodiment.

Figure 1:
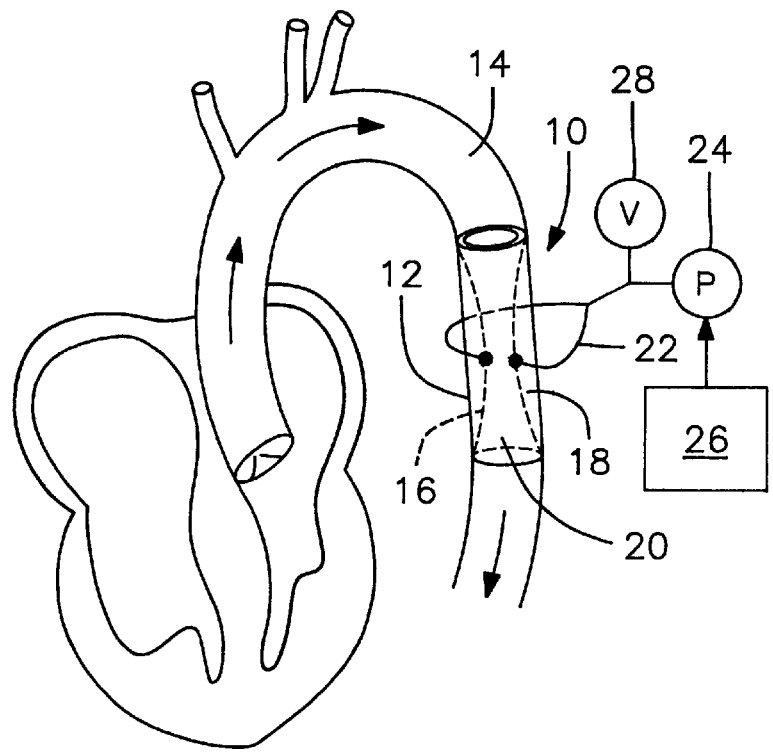
FIG. 1 is a diagrammatic view showing the heart-assist pump together with elements associated therewith and the environment in which said appliance is implanted

In FIG. 1, there can be seen an implantable heart assistance pump of a type that is itself known (e.g. from above-mentioned U.S. Pat. No. 522,980 or French application 96/00949), in which the main element 10 comprises a rigid body 12, typically in the form of a circular cylinder, that is open at both ends and that is inserted in the descending aorta 14, with the axis of the aorta and the axis of the body 12 coinciding, and with both these elements having substantially the same diameter.

The rigid body 12 contains a flexible membrane 16. In the embodiment shown, the shape of the membrane 16 at rest is similar to that of the body 12 so that it is a substantially close fit therein, and it is secured thereto at both ends around its entire periphery.

In this way, between the body 12 and the membrane 16, there is defined an intermediate space 18 that is closed and of variable volume, and inside the membrane 16, there is defined a central space 20, that is likewise of variable volume, with this volume decreasing when the volume 18 increases, and vice versa.

The volume of the space 18 is increased by injecting a hydraulic fluid (typically a biocompatible aqueous saline solution, e.g. a physiological serum) via one or preferably more points connected via a duct 22 to a variable pressure source 24 controlled by control electronics 26. Provision may advantageously also be made for a hydraulic fluid reservoir 28 in the form of a septum that is accessible percutaneously by means of a hypodermic needle to enable the volume and/or the salinity of the fluid to be adjusted, or to enable it to be emptied out.

Figure 2:
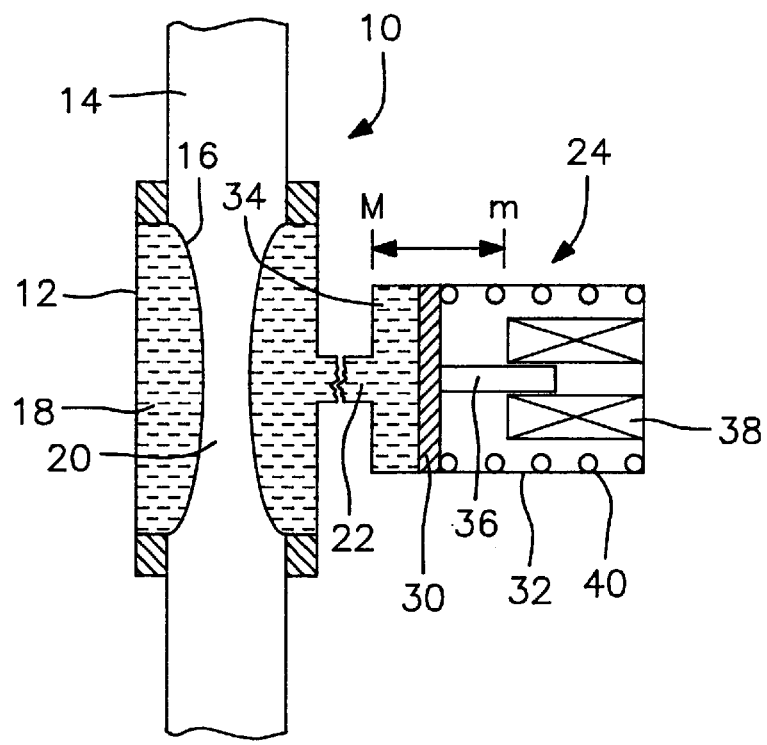
FIG. 2 is a diagrammatic view of the heart-assist pump and of the device of the invention, for explaining how these two elements co-operate.

The invention relates more particularly to the element 24, i.e. to the device for generating/regulating the pressure of the implanted system. FIG. 2 gives a theoretical diagram of the device 24. The device comprises a piston 30 that is movable in a cylindrical body 32 between two spaced-apart extreme positions M and m so as to define a variable volume 34 in fluid communication via the duct 22 with the space 18 of the pump, the volume of which space can therefore be varied to act on the membrane 16.

The position M corresponds to the maximum stroke of the piston, and thus to a minimum volume 34, to a maximum volume 18, and to maximum compression of the membrane 16. This extreme position corresponds to the end of heart diastole where the aortic pressure reaches its lowest value in the heart cycle. The other extreme position, m, corresponds to a maximum for the volume 34 and thus to a minimum for the volume 18; it is reached during systole, when the aortic pressure reaches its highest value in the heart cycle.

The piston 30 is driven via its shaft 36 which is itself driven by a motor 38, typically an electric motor driven by the electronics 26 as a function of various signals that have been picked up. The piston also receives the force delivered by a spring 40 bearing against its inside face and urging it towards its position of maximum displacement M.

The pressure exerted by the hydraulic fluid on the piston 30 is equal to the aortic pressure, while the influence of the inertia of the blood and of the fluid, of viscosity losses in said fluids, and of the elastic resistance of the membrane can be ignored since said influence is minimized by the architecture of the pump.

The operation of the device is explained below with reference to FIGS. 3 to 6.

Figure 3:
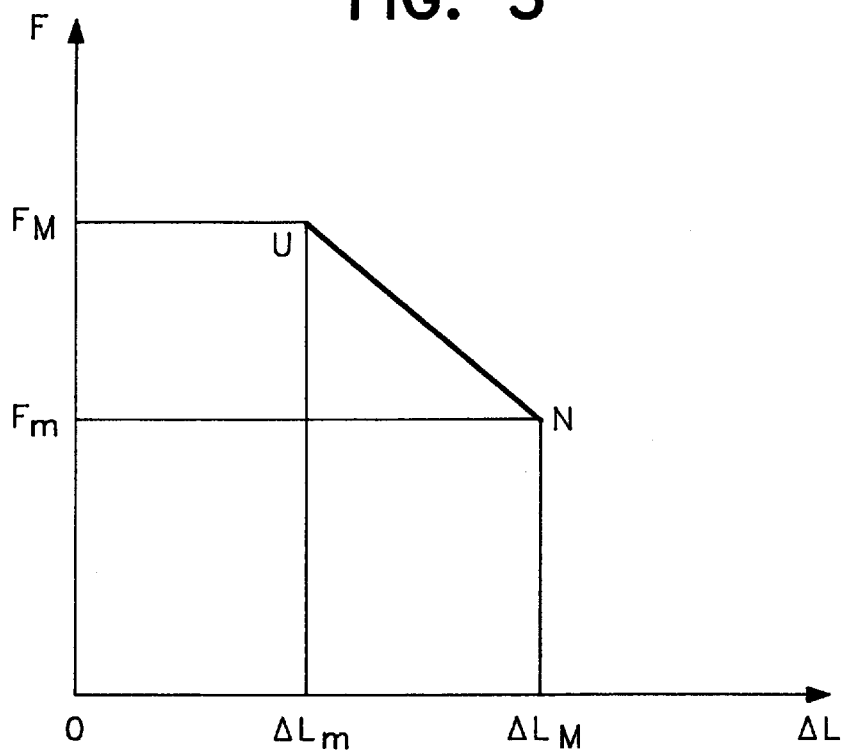
FIG. 3 shows the force/deformation characteristic of the compensation spring of the FIG. 2 device, when considered in isolation.

As a reminder, and to clarify the explanation, FIG. 3 shows the force/elongation (F/ΔL) characteristic of the spring 40 (which is assumed to be linear) considered on its own between two extreme values $\Delta L_m$ and $\Delta L_M$ corresponding respectively to the positions m and M shown in FIG. 2; the corresponding forces are $F_m$ and $F_M$.

Figure 4:
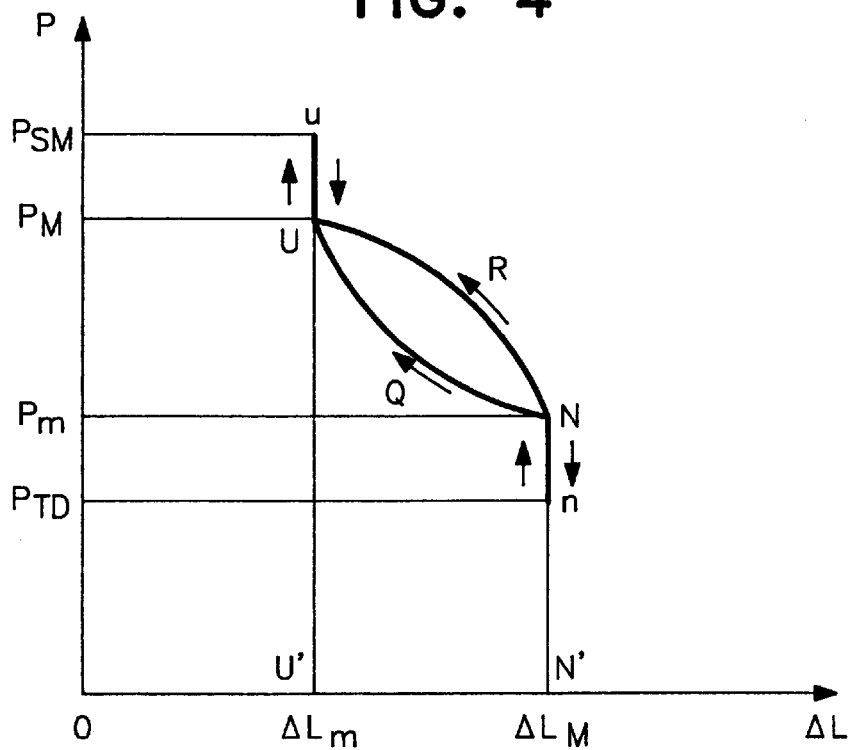
FIG. 4 is a characteristic showing the arterial pressure as a function of the displacement of the piston of the FIG. 2 device, in the absence of the compensation spring.
Figure 5:
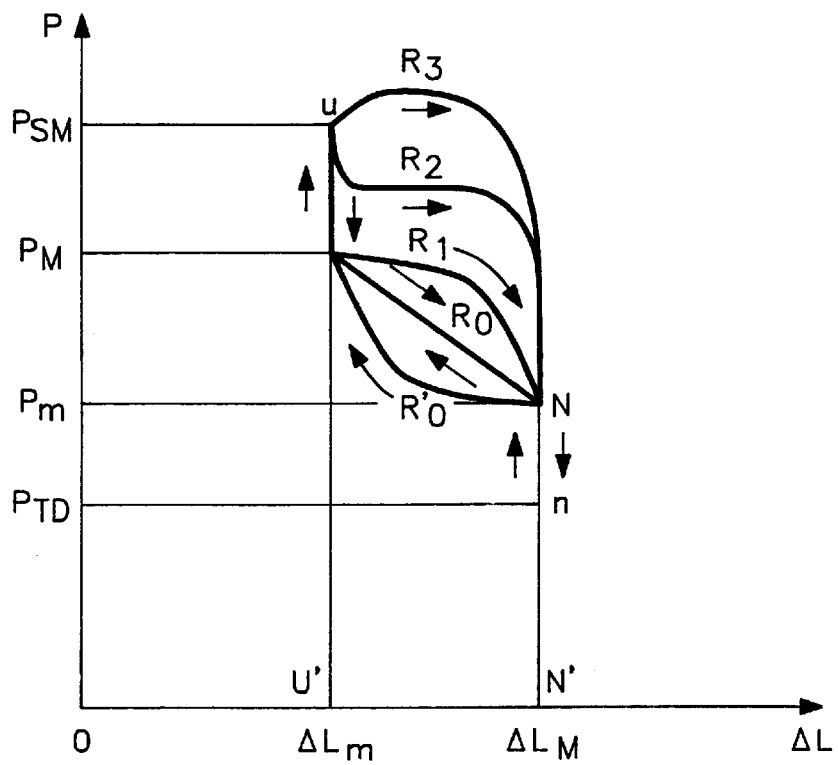
FIG. 5 is equivalent to FIGS. 3 and 4 combined, i.e. when the compensation spring is used in the device when in position.
Figure 6:
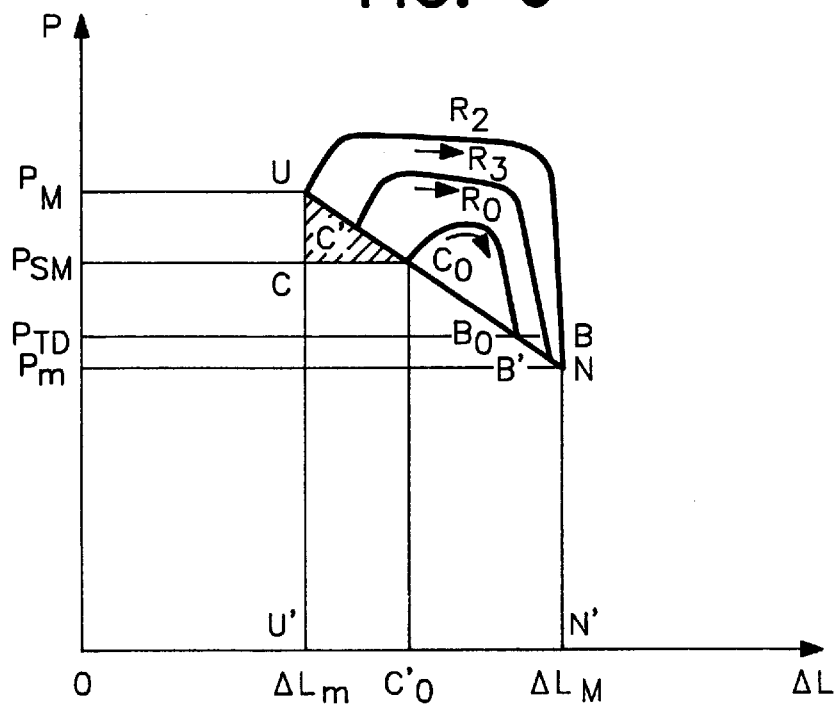
FIG. 6 is analogous to FIG. 5, for another implementation.

FIGS. 4 to 6 give the pressure P=F/Σ of the fluid exerted on the front face (of area Σ) of the piston 30 and thus substantially equal to the aortic pressure, and it gives said pressure as a function of the displacement ΔL of the piston between the above-mentioned extreme values $\Delta L_m$ and $\Delta L_M$.

The operation of the device should initially be considered ignoring the spring 40 (FIG. 4): at the end of diastole and at the beginning of systole, the operating point of the piston is situated at n. During the systolic phase, arterial pressure goes from a value $P_{TD}$, the lowest telediastolic pressure of the cycle, to a value $P_{SM}$ which is the highest systolic pressure, following the path nNQUu. Between the points N and U the piston moves from one end to the other, from $\Delta L_M$ to $\Delta L_m$, while between n and N, and between U and u, it does not move.

The energy delivered to the blood by the device is represented by the area of the loop N'nNQUuUU'N', which is equal to the area of the loop N'NQUU'N'. Diastole produces the reverse travel returning the operating point to its initial point n via the path uURNn. In manner similar to the preceding manner, the energy supplied by the device to the blood is represented by the area of the loop U'URNN'U'.

In FIG. 4, the energy balance of a cycle, corresponding to the net energy supplied by the device to the blood, is equal to the area of the loop NQURN (if the loop were to be followed counterclockwise, then it would be the blood supplying the corresponding amount of energy to the device).

The difficulty for the device, from the point of view of its own energy balance, is that losses should be minimal, which problem becomes particularly difficult to resolve since the amounts of energy interchanged are significantly greater than the differential energy that is transferred. An electro-mechanical device having an electric motor, e.g. an electromagnet, or a rotary motor associated with a mechanism for converting rotary motion into linear motion, will develop work on path URN with quite good efficiency, e.g. 0.8, with loss proportional to the area of U'URNN', and it will recover energy in the opposite direction following the path NQU with significantly worse efficiency, e.g. 0.5, with loss being proportional to the area N'NQUU'.

Consequently, the energy balance is very poor. Writing $W_Q$ for the energy picked up and $W_R$ for the energy delivered, the energy picked up is:

$$e_Q = \rho_1 W_Q$$

where $\rho_1 = 0.5$
and the energy expended is:

$$e_R = W_R / \rho_2$$

where $\rho_2 = 0.8$

If $W_R = 1.2\ W_Q$, a practical situation for the intended application, then the differential work obtained is $0.2\ W_Q$ for the following energy balance:

$$e_R=e_Q=(1.2\ W_Q/0.8)-0.5\ W_Q=W_Q$$

while the energy delivered is 0.2 $W_Q$. The efficiency of the operation is $(0.2\ W_Q)/W_Q=0.2$.

If the pressure $P_{SM}$ and $P_{TD}$ are such that $P_{SM}<P_M$ and/or $P_{TD}>P_m$, then the differential work loop that results therefrom would be limited by u and/or n instead of U and N, but the reasoning would be similar and the result would be identical.

The device of the invention proposes the following solution.

Taking into consideration the reciprocating motion of the piston during the cycle, as it passes from operating point N to point U, the force communicated to the piston can be obtained from two forces acting in series on the axis of the piston:

1) An elastic passive element, e.g. the helical spring 40 as shown in FIG. 2, which stores and restores the major fraction of the energy that is interchanged. When the spring is provided in the system, the overall characteristic thereof is altered and becomes a combination of the characteristics of FIG. 3 (spring on its own) and of FIG. 4 (the system without a spring).

This overall characteristic is shown in FIG. 5:

the operating point of the spring goes from N to U along path $R_0$ in the direction $NR_0U$ on systole and $UR_0N$ on diastole. This path is rectilinear if the spring is linear, and its shape may differ slightly if the spring is not linear, with no consequence on operation. The advantage of the spring is that its energy balance is close to 1.

2) An electromechanical element provides the forces necessary for modifying the looped path between N and U. For example, in FIG. 5, the path $nNR_0Uu$ is unchanged for systole, and the path $uUR_1Nn$ is unchanged for diastole, forming a loop $NR_0R_1N$ which represents the work transmitted directly by the electromechanical element to the piston, i.e. to the blood, independently of the energy that is interchanged which corresponds to the area of the loop $U'UR_0NN'U'$, which interchange is supported by the spring on its own.

Consequently, the energies involved with operation of the motor are much less than they were in the case shown in FIG. 4, so losses are reduced, as are the dimensions of the motor, and the problem of recovering energy at low efficiency no longer arises. To understand the mechanism of going from the path $UR_0N$ to the path $UR_1N$, it should be observed that the second path is followed in shorter time than the first, with the increase in pressure giving rise to an increase in the displacement speed of the piston and by an increase in the instantaneous diastolic flow rate of the aorta.

To conclude, on the bases of the example explained above, for transmitted work of 0.2 $W_Q$ and for energy consumption of:

$$e_R=(0.2\ W_Q)/0.8=0.25\ W_Q$$

overall efficiency becomes:

$$\rho_G=(0.2\ W_Q)/(0.25\ W_Q)=0.8$$

which value should be compared with the efficiency of 0.2 in the preceding case.

In a variant of the above-considered case, FIG. 5 shows other paths corresponding to increasing energies delivered by the device to the blood: paths $UR_2N$, $UR_3N$ resulting from force added to that of the spring showed by the pressure difference between the path $uR_3N$, for example, and the path $UR_0N$ which is that of the spring. It is also possible for the electric motor to correct the systolic process, following the path $NR'_0U$ instead of $NR_0U$, the electric motor delivering work corresponding to the area of the loop $NR'_0UR_0N$ which is subtracted from the work of the spring, with the balance giving rise to less energy taken by the blood, corresponding to the area $N'NR'_0UU'$. Naturally, this path is undesirable from the energy balance point of view for the device, but it can be desirable for other reasons. The shape of the loop is determined in the end as a compromise between various conditions of physiological, energy, mechanical, and electrical natures.

In another variant, FIG. 6 shows the case where $P_{SM}<P_M$ and $P_{TD}>P_m$. In this case, the free travel of the spring without assistance from the motor is $B_0C_0$, thus limiting the stroke of the piston. The contribution of the motor can be expressed by the diastolic path $C_0R_0B_0$, without modifying the stroke of the piston.

Nevertheless, the motor can return the stroke of the piston to the corresponding end $\Delta L_m$, by displacing the position of the piston from $C_0$ to U at the end of diastole. To perform this displacement, the motor exerts a force that increases from 0 at $C_0$ to $P_M-P_{SM}$ at U, thereby delivering work as represented by the area $C_0CUC_0$, with the blood supplying the work corresponding to the area $C'_0C_0CUC'_0$.

In identical manner, the point $B_0$ can be brought back to the end N by means of work supplied by the electric motor and represented by the area $B_0BN$. In this way, by using additional energy represented by the sum of the two triangular areas $C_0CU$ and $B_0BN$, the device can transfer to the blood an amount of energy which corresponds to the area $NUR_2N$. The operation which consists in increasing the amount of energy transferred to the blood from the value corresponding to the area $B_0C_0R_0B_0$ to the value corresponding to the area $NUR_2N$ can be performed under good conditions of energy efficiency in spite of the mismatch between the spring and the dynamic range of arterial pressure as represented by $P_{TD}/P_{SM}$, where the spring is too stiff.

Finally, it will be observed that in the same manner, the positions of the piston can be brought to intermediate points C' between $C_0$ and U, and B' between $B_0$ and N, thereby giving rise to a diastolic path $C'R_3B'$.

Finally, it should be observed that there exists a case where only the elasticity of the spring is required by the device, without any net transfer of energy to the blood. This applies when it is desired to reduce the postcharge on the left ventricle by increasing the apparent elasticity of the aorta by increasing the systolic ejection of the left ventricle by means of the volume stored by the piston during systole. The device is then simplified by omitting the electric motor. The device is then passive and can, for example, be fitted to an aortic prosthesis which, because of the increased apparent elasticity given thereto by the device, is capable of providing the important advantage of decreasing postcharge on the heart, and consequently of decreasing systolic tension.

Figure 7:
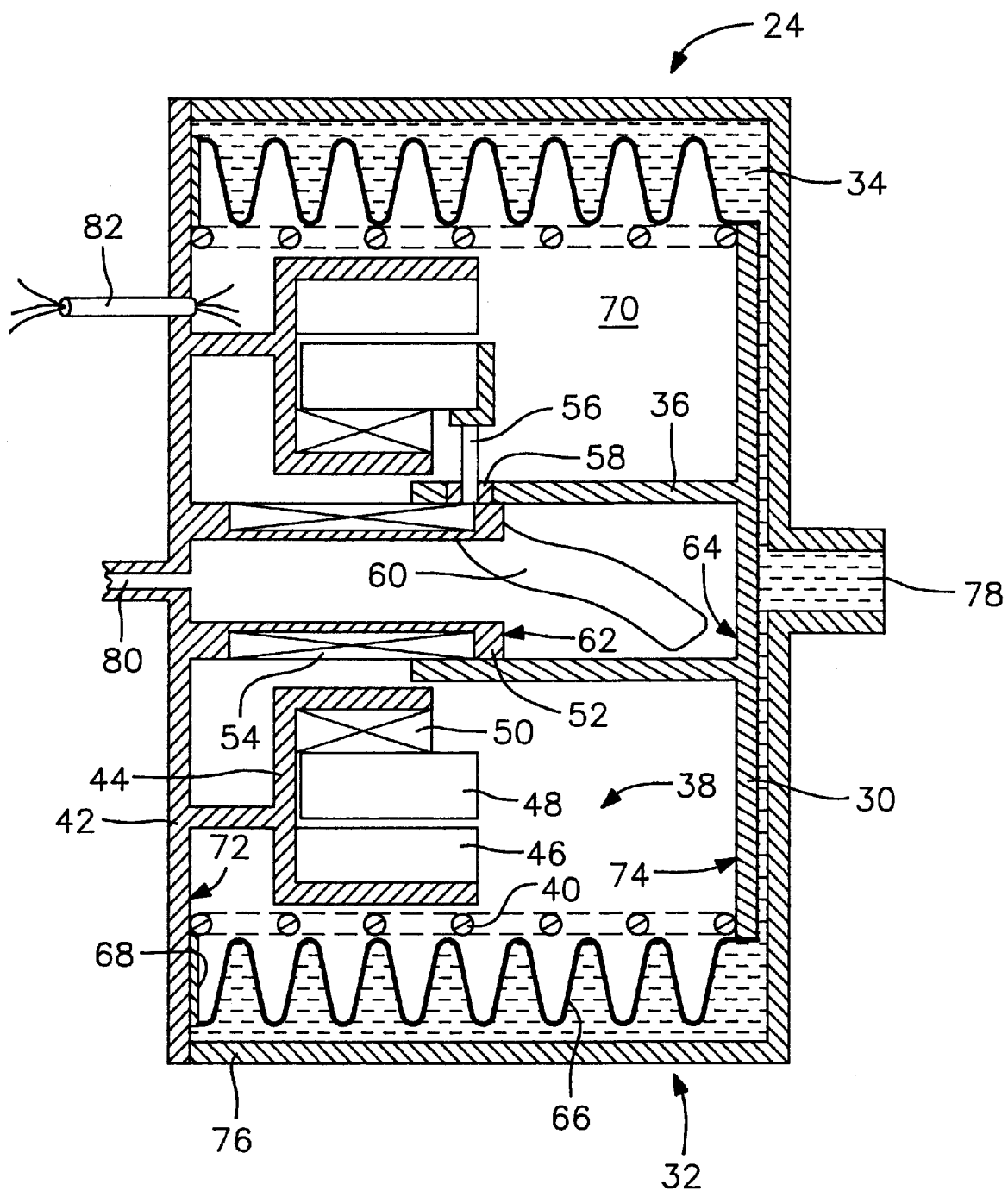
FIG. 7 is a more detailed view showing the internal structure of the device of the invention in section.

FIG. 7 is a section through an embodiment of a structure suitable for the pressure generator/regulator device 24.

In this embodiment, the body 32 is in the form of a substantially cylindrical housing whose posterior face is a plate 42 provided on the inside with a support 44 for the electric motor 38, which motor essentially comprises a stator 46 and a rotor 48 mounted on circular ball bearings 50. The motor is advantageously a brushless torque motor type of electric motor controlled by electrically switching the coils of the stator. Rotation of a motor of this type (and thus operation of the device) can be controlled very precisely, and the motor can also be provided with displacement sensors, e.g. of the Hall effect type or optical sensors, making it possible to know very accurately the angular position of the rotor relative to the stator, and thus, as explained below, the position of the piston 30.

In the axial position, the end wall 42 carries a cylindrical guide tube 52 on which the piston rod 36 slides, the piston rod is preferably in the form of a hollow tube, and sliding between the tube 36 and the guide 52 is facilitated by linear ball bearings 54.

The rotor 48 is secured to a radial finger 56 that extends inwards, carrying at its end a wheel 58 which engages in a helical groove 60 formed in the rod 36.

In this manner, the motion of the rotor causes the rod 36 to be moved axially together with the piston 30 because of co-operation between the wheel 58 and the helical groove 60.

The dimensions of the various elements, and in particular the pitch of the helical groove 60, can be selected so that transmission is reversible, i.e. so that not only does displacement of the rotor cause the rod 36 of the piston to move in translation, but also, in the opposite direction, force on the piston (due to the pressure exerted on its face in contact with the hydraulic fluid) is not blocked by the assembly comprising the groove and the wheel.

The rearward displacement of the piston 30, i.e. its displacement towards the end plate 42, is limited by the front face 62 of the guide 52 coming into abutment against the inside face 64 of the piston 30.

The piston proper 30 forms a portion of an assembly that includes, in particular, a bellows 66 bonded to the periphery of the piston at its front end and terminated, at its other end, by a disk 68 for fixing against the end wall 42 in leakproof manner. The assembly formed by the piston 30, the bellows 60, and the end wall 42 defines a chamber 70 which is isolated from the external environment, and in particular from the volume 34 situated between said piston-and-bellows assembly and the remainder of the body 32 and containing the hydraulic fluid. The helical spring 40 is located in this closed volume 70 and it has one of its ends bearing at 72 against the inside face of the end wall 42, and its other end bearing at 74 against the inside face of the piston 30.

The spring 40 provides the major portion of the elastic component of the device with the advantage described above with reference to FIGS. 5 and 6, and the bellows 66 (which may optionally be a metal bellows) may optionally play an additional elastic role.

Means (not shown) may possibly be provided for adjusting the compression of the helical spring 40 by offsetting its rear end relative to the internal face 72 of the end wall 42 against which it bears. This offset may be provided by a disk pressed against the end of the spring and secured to a rigid sleeve disposed inside the helical spring and in the immediate vicinity thereof, being displaced axially by means of an electrical micromotor so as to adjust and optimize the operating range of the elastic element as a function of arterial tension.

The side and front walls of the body 32 are constituted by a cover 76 pressing against the end wall 42 so as to define the volume 34 which is filled with hydraulic fluid, said cover being provided with a mouth 78 connected to the pump, as shown in above-mentioned FIG. 2.

The inside volume 70 of the piston-and-bellows assembly is filled with air or with a controlled-atmosphere gas, and it may be connected via a nozzle 80 to a reference pressure chamber whose pressure is maintained very close to atmospheric pressure.

Finally, a multiconductor electrical cable 82 feeds electricity to the motor and conveys data, in particular measurement data concerning displacement of the piston.

In a simplified variant of the above-described device, it is possible to omit the electric motor 38 and its support 44, the tube 52, and the hollow shaft 36. The remaining parts are essentially the end wall 42 fitted with a nozzle 80, the housing 76 fitted with the mouth 78, the bellows 66, and the helical spring 40.

Under such circumstances, the device is passive. The assembly 10 has the same structure as in the preceding case, however functionally it is no longer a genuine "pump" but is merely an aortic prosthesis, with the device of the invention acting as an artificial elastance connected to said aorta prosthesis, and with the heart supplying all of the energy demand on its own.

In this variant, the simplified device makes it possible to compensate for hardening of the arteries, the artificially increased elasticity of the arterial system avoiding demanding excessive power from the ventricle to overcome the load represented by the inertia and the resistance of the blood column that it is to put into motion, thus making it possible to achieve improved hemodynamice for given energy.

Incidentally, it should be observed that the above remarks also apply to a complete device, i.e. to a motorized device, while it is not being powered, e.g. during rest phases, during which there is no need for additional energy to be provided to the heart in order to meet the needs of the organism. It can be seen that even in this configuration where the motor is stopped, the mere presence of the device provides benefit by artificially increasing the elasticity of the aorta.

I claim:

1. A pressure generator/regulator device (24) for an implantable heart-assist pump (10) of the back-pressure balloon type, said pump having variable volume means inserted in an artery, in particular the descending aorta, and making it possible to modify cyclically and in controlled manner a volume (20) through which the blood flows in this location,
   the device being characterized in that it includes a deformable enclosure (34) in fluid communication with said variable volume (20), and spring-forming means (40) for urging the deformable enclosure against an increase of volume resulting from an increase in pressure in said variable volume, and correspondingly in the enclosure, so as to provide additional elastance to the artery during the heart cycle.

2. The device of claim 1, in which the deformable enclosure is defined by a piston (30) movable in a body (32), the spring-forming means (40) urging the piston in the body in its direction for reducing the volume of the enclosure, and the piston is movable between two positions, a maximum volume position (m) associated with maximum compression of the spring, and a minimum volume position (M) associated with minimum compression of the spring.

3. The device of claim 1, further comprising motor means (38) for urging the deformable enclosure in controlled manner in the direction for increasing the volume of the enclosure or in the opposite direction, and exerting its action in addition to or in opposition to the action of the spring-forming means during the systolic phase and the diastolic phase of the heart cycle.

4. The device of claim 2 taken in combination, in which the motor means (38) are disposed inside the body, and comprise a rotary motor (46, 48) co-operating with a rod (36) secured to the piston via a transmission (56, 58, 60) reversibly transforming the rotary motion of the rotary motor into linear translation motion of the rod.

5. The device of claim 4, in which the transmission has a radial finger (56, 58) secured to the rotor of the rotary motor and co-operating with a helical groove (60) formed in a cylindrical element of the piston rod.

6. The device of claim 4, in which the rotary motor (46, 48) is an electric motor of the torque motor type.

7. The device of claim 4, in which the body (32) houses a sealed assembly with a rigid front wall forming said piston (30) and a side wall in the form of a bellows (66), said sealed assembly itself enclosing the rod of the piston (36), the rotary motor (46, 48), the transmission (56, 58, 60), and the spring-forming means (40).

* * * * *